United States Patent
Rashidi (10) Patent No.: US 6,728,563 B2
(45) Date of Patent: Apr. 27, 2004

(54) ELECTROPHYSIOLOGY/ABLATION CATHETER HAVING "HALO" CONFIGURATION

(75) Inventor: Rassoll Rashidi, Lakwood, OH (US)

(73) Assignee: St. Jude Medical, Daig Division, Inc.

( * ) Notice: Subject to any disclaimer, the term of this patent is extended or adjusted under 35 U.S.C. 154(b) by 0 days.

(21) Appl. No.: 09/726,235

(22) Filed: Nov. 29, 2000

(65) Prior Publication Data

US 2002/0065514 A1 May 30, 2002

(51) Int. Cl.⁷ .................................................. A61N 1/05
(52) U.S. Cl. ........................ 600/374; 607/122; 606/41; 600/381
(58) Field of Search ........................... 606/41; 607/122, 607/125; 600/374, 381

(56) References Cited

U.S. PATENT DOCUMENTS

| | | |
|---|---|---|
| 4,920,980 A | 5/1990 | Jackowski |
| 4,960,134 A | 10/1990 | Webster, Jr. |
| 5,125,896 A | 6/1992 | Hojeibane |
| RE34,502 E | 1/1994 | Webster, Jr. |
| 5,354,297 A | 10/1994 | Avitall .......................... 606/45 |
| 5,462,527 A | 10/1995 | Stevens-Wright et al. |
| 5,588,964 A | 12/1996 | Imran et al. |
| 5,611,777 A | 3/1997 | Bowden et al. |
| 5,656,029 A | 8/1997 | Imran et al. |
| 5,673,695 A | 10/1997 | McGee et al. .............. 128/642 |
| 5,715,817 A | 2/1998 | Stevens-Wright et al. |
| 5,755,760 A | 5/1998 | Maguire et al. ............. 607/122 |
| 5,807,249 A | 9/1998 | Qin et al. |
| 5,820,591 A | 10/1998 | Thompson et al. ............ 604/95 |
| 5,861,024 A | 1/1999 | Rashidi ....................... 607/122 |
| 5,935,102 A | 8/1999 | Bowden et al. |
| 5,938,694 A | 8/1999 | Jaraczewski et al. ........ 607/122 |
| 5,944,690 A | 8/1999 | Falwell et al. |
| 5,987,344 A | 11/1999 | West |
| 6,002,955 A | 12/1999 | Willems et al. .............. 600/374 |
| 6,183,463 B1 | 2/2001 | Webster, Jr. |
| 6,308,090 B1 * | 10/2001 | Tu et al. ...................... 607/122 |
| 6,325,797 B1 * | 12/2001 | Stewart et al. .............. 607/122 |
| 6,356,790 B1 * | 3/2002 | Maguire et al. ............. 607/113 |

* cited by examiner

Primary Examiner—Lee Cohen
Assistant Examiner—Henry M. Johnson, III
(74) Attorney, Agent, or Firm—Fay, Sharpe, Fagan, Minnich & McKee, LLP (57) ABSTRACT

A remotely bi-directional deflectable electrophysiology/ablation catheter of the type intended for placing into an interior passage of the heart is disclosed. The distal end of this elongated tubular catheter has a pair of tension/compression members each with a flattened end portion connected to the distal electrode and extending through the catheter casing and attached to a user moveable actuator for effecting the tension/compression thereon for remotely curling the distal end of the catheter. Spaced ring electrodes are provided adjacent the distal electrode. A permanent bend is pre-formed in the casing and tension/compression members adjacent the ring electrodes about an axis perpendicular to the elongated tension/compression members. Movement of the remote actuator causes the distal portion of the catheter to curl into a "halo" in a plane perpendicular to the axis along the elongated catheter casing, thus permitting electrical mapping or ablation with the distal and/or ring electrodes about the inner surface of the heart passage into which the "halo" is formed and situated.

13 Claims, 12 Drawing Sheets

ELECTROPHYSIOLOGY/ABLATION CATHETER HAVING "HALO" CONFIGURATION

CROSS REFERENCE TO RELATED APPLICATIONS

None

STATEMENT REGARDING FEDERALLY SPONSORED RESEARCH OR DEVELOPMENT

Not Applicable

MICROFICHE APPENDIX

Not Applicable

BACKGROUND OF THE INVENTION

The present invention relates to a catheter employed for diagnostic and/or therapeutic procedures in medicine, more specifically in minimally invasive cardiac electrophysiology studies and/or cardiac ablation procedures.

Catheters of the above described type are known in the art and, in particular, catheters capable of bi-directional curvature or lateral deflection upon movement of a remote manual actuator. A catheter of the aforesaid type employing tension/compression members without the need for a compression strut is known; and, in particular such a catheter is shown and described in my earlier U.S. Pat. No. 5,861,024 commonly owned by the assignee of the present invention. The catheter described in the aforesaid patent '024 is of the type that is bi-directionally curveable in a generally planar curvature for entering the passages of the heart. In certain procedures the catheter is inserted through the femoral vein to a first chamber of the heart and it is then desired for the end of the catheter employing the electrodes to enter into another passage of the heart communicating with the first chamber of the insertion.

In addition, it has been desired to have the catheter conform to the inner periphery of certain passages in the heart and in particular the pulmonary vein for mapping or taking of electrical measurements of the condition of the inner periphery of the aforesaid passage or, in certain cases, performing ablation procedures on the passage of the heart.

Heretofore, it has been possible to deflect the catheter laterally with respect to the direction of elongation of the catheter casing; however, it has not been possible to provide such a catheter which could conform to the transverse peripheral configuration of the interior of the heart passage for which it is desired to conduct these studies and/or ablation procedures. Thus, it has been desired to find a way to map the inner periphery of the passage of the heart in a circumferential or transverse direction with a remotely inserted and remotely actuate deflectable tip catheter.

SUMMARY OF THE INVENTION

The present invention provides a solution to the above-described problem of utilizing a remotely insertable and deflectable tip catheter in a passage in a human heart and deflecting the distal end of the catheter in a substantially halo, loop, or lariat configuration of curvature in a plane generally perpendicular to the direction of elongation of the catheter. In other words, the distal end of the catheter is curved in a planar curvature about an axis, which is parallel to the direction of elongation of the catheter casing.

The catheter of the present invention employs tension/compression members anchored to the distal end of the catheter and which extend through the catheter casing to the proximal end and which are connected to an actuator for manually applying tension to one of the tension/compression members while compressing the other for remotely affecting the curvature of the distal end of the catheter when the catheter is inserted typically through the femoral vein into a passage in the heart.

The catheter of the present invention has a plurality of spaced electrodes disposed on the distal end of the casing of the catheter; and, each of these electrodes has an electrical lead connected thereto which extends through the casing to the proximal end of the catheter for external electrical connection thereto.

The catheter casing and tension/compression members have a permanent bend or preformed bend of about a right angle formed adjacent the proximal-most electrode; and, this pre-formed bend remains in the casing as the catheter is deflected and inserted through a guide tube placed in the vein for entry into the heart passage. Upon user movement of the remote actuator, which affects movement of the tension/compression members inside the casing, the distal end of the catheter deflects laterally or curls into a "halo" configuration in a plane generally at right angles to the direction of elongation of the catheter, or in other words, in a plane parallel to the axis of curvature of the pre-formed bend, which axis is at right angles to the direction of elongation of the catheter casing. The halo is capable of extending in curvature through an angle of at least 270° and thus disposes the electrodes transversely or circumferentially at a single station about the major portion of inner periphery of the passage in the heart. This disposition of the electrodes enables an electrical mapping of the inner periphery of the heart passage or the performance of ablation procedures at spaced intervals about the circumference of the interior of the heart passage. Upon reversal of the remote manual actuator attached to the proximal end of the catheter casing, the halo is uncurled to a straight configuration. The catheter may then be removed from the heart passage through the guide tube in vein, usually the femoral vein, from which it was inserted. In the preferred embodiment of the invention the initial permanent or pre-formed bend in the casing is formed at about 90° in catheters having the minimum radius for the curled loop and about 450° for catheters having a larger curled loop.

The catheter of the present invention has the permanent or pre-formed bend therein about an axis perpendicular to the direction of elongation of the catheters; and, the portion of the catheter distal the pre-formed bend is preferably manually flexed and inserted into the vein for entry into the heart passage. The pre-formed bend remains formed in the catheter. Upon user movement of the remote actuator, flexure of the catheter is facilitated in a plane normal to the direction of elongation of the catheter casing to thereby form a "halo" for facilitating circular electrical mapping of the interior of the heart passage into which the halo is situated.

DETAILED DESCRIPTION OF THE INVENTION

Figure 1A:
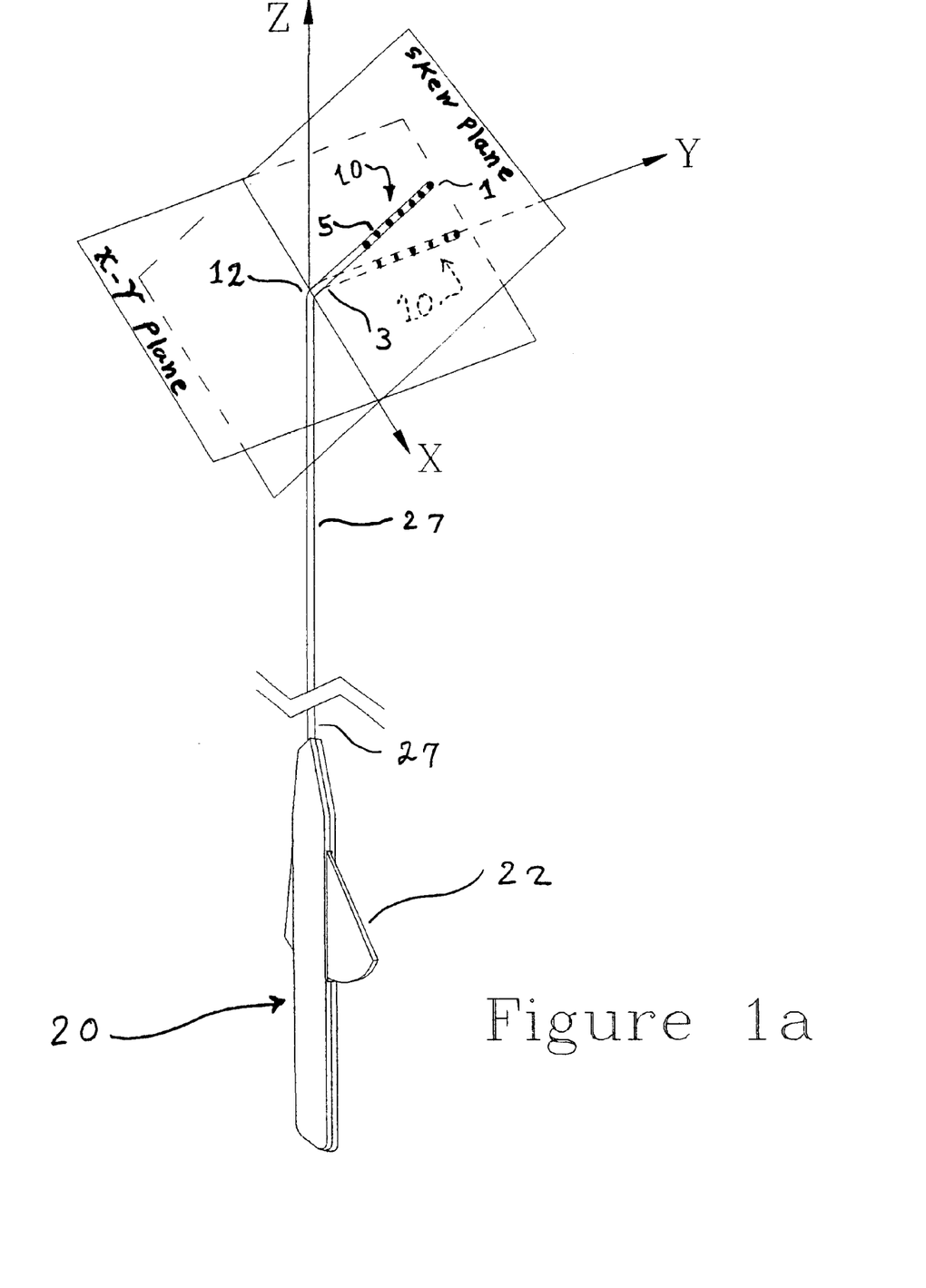
FIG. 1a is a perspective view of the distal end of the catheter of the present invention having the pre-bend formed therein.
Figure 1B:
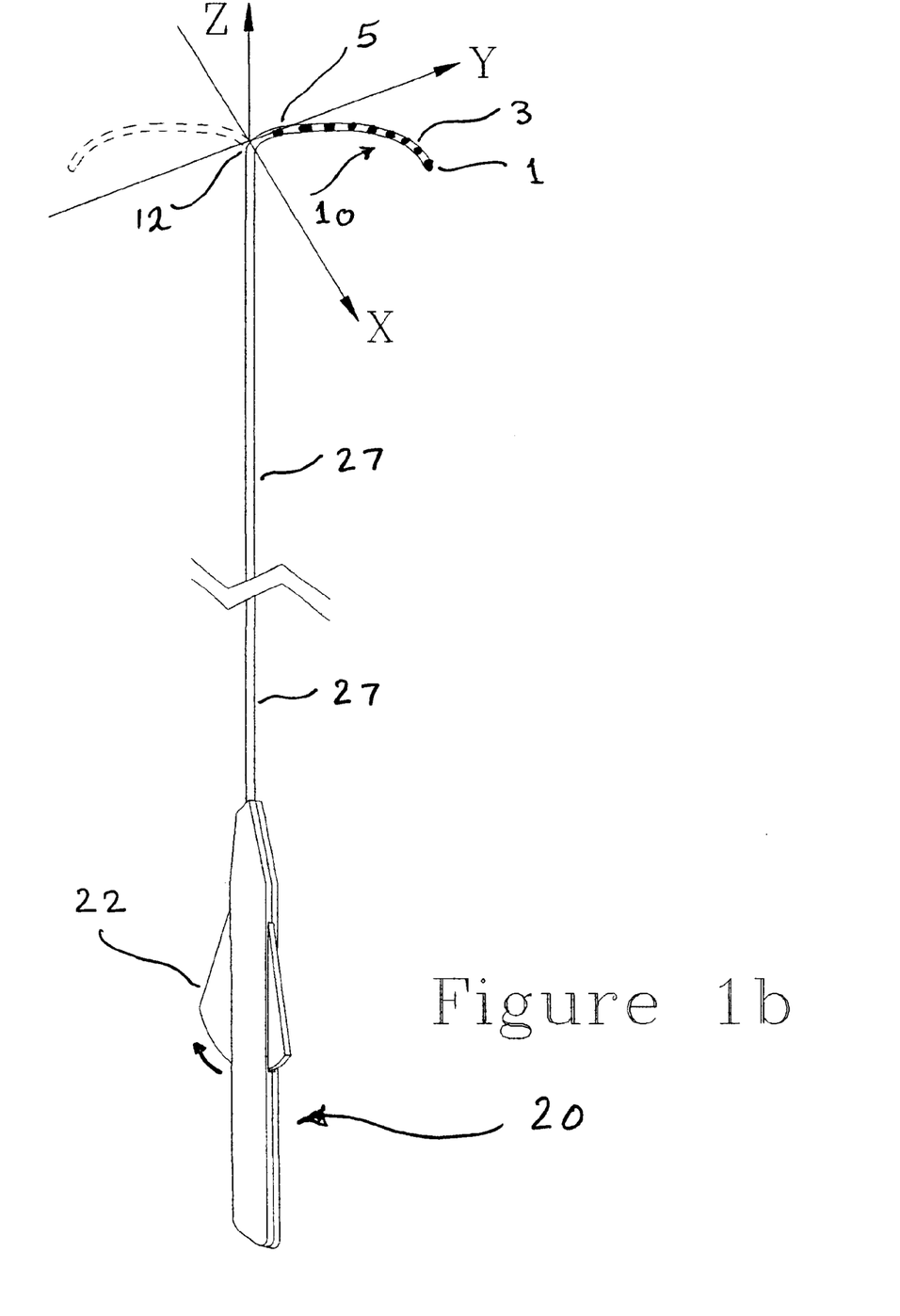
FIG. 1b is a view similar to FIG. 1a showing the distal end of the catheter partially curved by actuation from the proximal end.
Figure 1C:
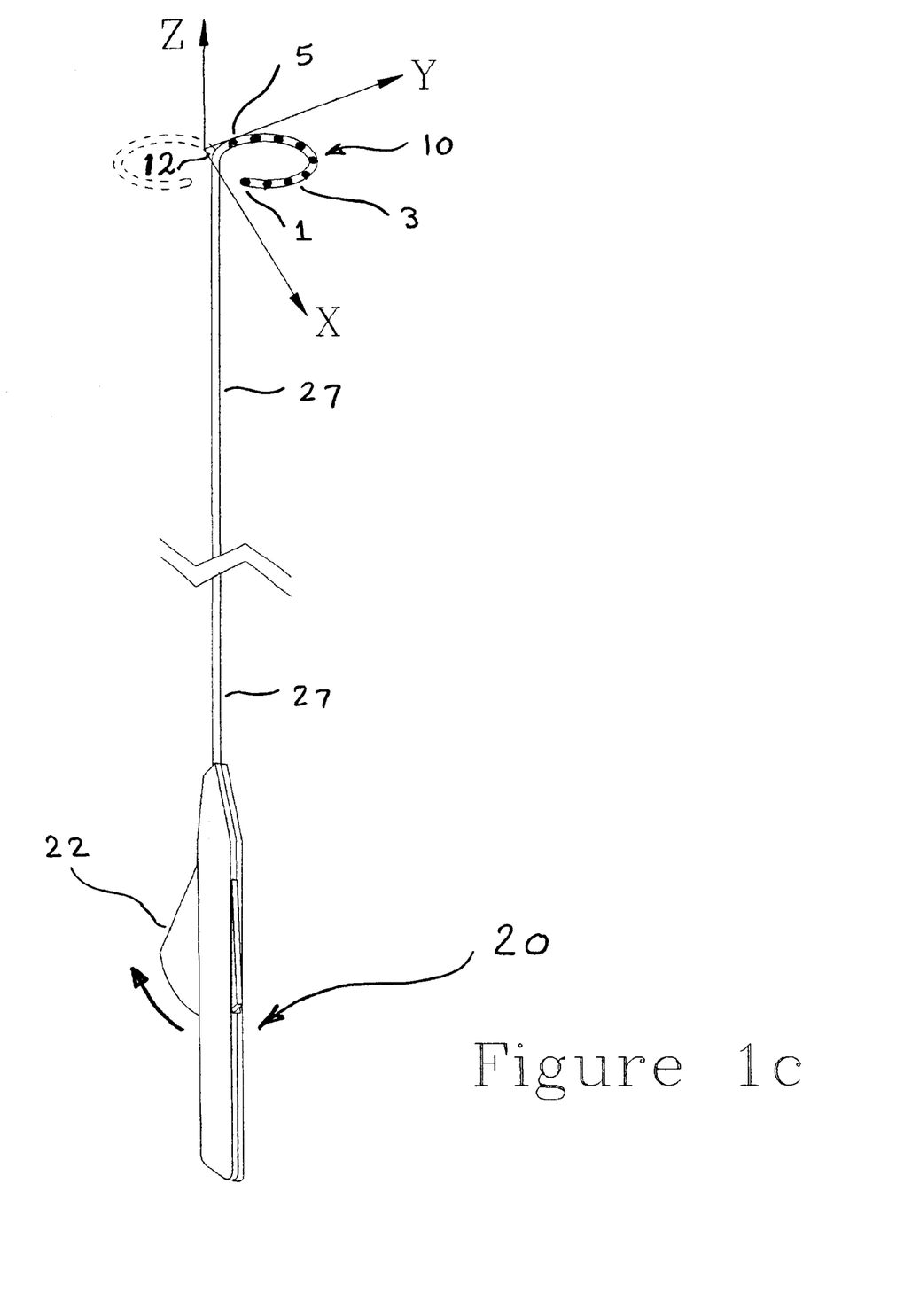
FIG. 1c is a view similar to FIG. 1b showing the catheter further deflected from the position of FIG. 1b by actuation from the proximal end to form a completed halo of at least 270°.

Referring to FIGS. 1a through 1c, the distal portion of the catheter is indicated generally at 10 and has a tubular flexible outer casing 3 with a distal end electrode 1 and a plurality of spaced electrodes 5 disposed thereon and preferably having an annular or ring shaped configuration. An initial permanent or pre-bend indicated generally at 12 is formed in the region adjacent the proximal-most one of the distal ring electrodes 5. In the presently preferred practiced, the pre-bend 12 is formed about the X axis and is formed to angle of about 90° and preferably about 83° for a casing of about 1.6 mm diameter (6 French) and for a minimum radius of 5 mm for the halo as shown in dashed outline in FIG. 1a. In the present practice of the invention for a catheter casing 3 having a diameter of about 1.6 mm (6 French) and a halo curled at 15 mm radius, a pre-formed bend 12 of about 45 degrees, as shown in solid outline in FIG. 1a, has been found satisfactory.

It would be understood that the details of actuator for the proximal end of the catheter have been omitted in FIGS. 1a through 1c for ease of illustration. However, the operation of the internal components of the catheter for affecting the flexing or curling for the halo as shown in FIGS. 1b and 1c will be described hereinafter. In this presently preferred practice, the actuator is of the type shown and described in my earlier U.S. Pat. No. 5,861,024.

Figure 2:
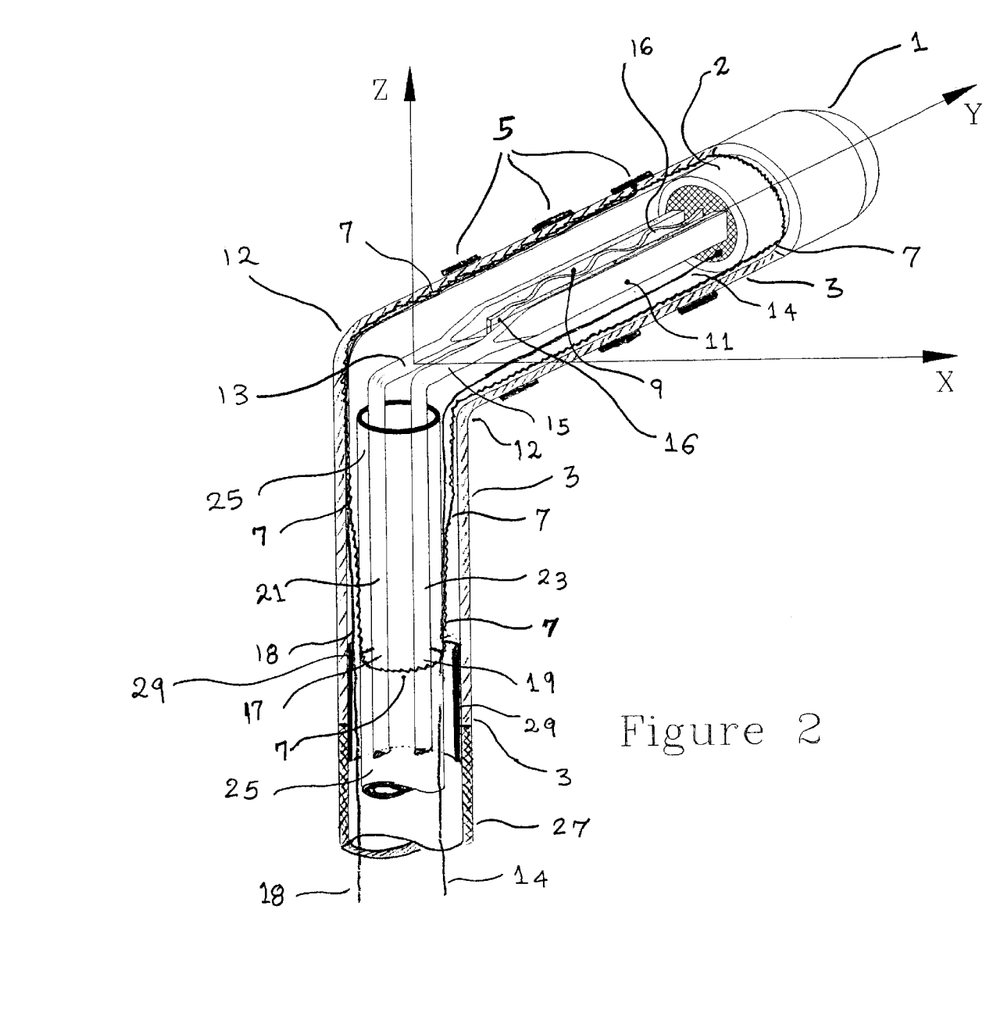
FIG. 2 is a perspective view of the distal end of the catheter after forming of the preformed bend with portions of the casing removed to show the interior components thereof.

Referring to FIG. 2, the flexible tubular casing of the catheter is shown denoted by reference numeral 3 has the ring shaped electrodes 5 disposed there over in axially spaced arrangement and spaced from the distal-most or tip electrode 1. The tip electrode 1 has a reduced diameter portion denoted by reference numeral 2 which has flattened end portions 9, 11 of the tension/compression members 13, 15 attached hereto. The portions 13, 15 have circular transverse sections, as do the portion 21, 23 extending through the casing on the opposite side of the pre-formed bend 12 and through the casing to the proximal end of the catheter for attachment to an actuator. The flattened ends 9, 11 of the tension/compression members 13, 15 are disposed in laterally spaced generally parallel arrangement with a resilient flexible spacer in the form of a laterally resilient wave-spring denoted by reference number 16 disposed there between.

The flattened ends 9, 11 of the tension/compression members are preferably attached to the portion 2 of the distal electrode 1 by weldment such as, for example, brazing and thereby forming a kinematic junction at the distal electrode 1 with the tension/compression members 13, 15.

The tension/compression members 13, 15 have on the proximal side of the pre-formed bend 12 a plastic sheath or tubing 25 received there over; and, in the present practice of the invention the tubing is formed of polyamide plastic material. However, it will be understood that alternatively other suitable plastic materials or a closely wound spring may be employed for the sheath or tubing 25.

The tip electrode 1 and each of the ring electrodes 5 has an electrical lead attached thereto which lead extends through the casing 3 to the proximal end of the catheter as denoted respectively by the electrical lead 14 for the distal electrode 1; and, a typical lead for the ring electrodes 5 is denoted by reference numeral 18.

The flattened portions of the tension/compression members 9, 11 and the portions 17, 19 in the pre-formed bend and the end of the tube 25 are covered with a flexible shrink tube as denoted by reference numeral 7.

A bushing 29 is received over the end of the shrink tube 7; and, the bushing 29 has attached thereto a braided sheath or exterior tube denoted by reference numeral 27. Sheath 27 has the distal end thereof abutted with casing 3; and, the opposite end extends to the proximal end of the catheter. The end of the bushing 29 opposite the braided sheath 27 on the distal end thereof is inserted within and attached to the proximal end of the non-braided casing 3.

In the present practice of the invention, the sheath or tube 25 is formed of plastic material such as polyamide plastic and extends to the proximal end of the braided exterior tube 27; however, it will be understood that the tube material is not limited to polyamide and may be formed of other suitable thermo-plastic materials or a closely wound spring which may be made from stainless steel wire.

In the present practice of the invention, it will be understood that the pre-formed bend 12 is permanently formed in the catheter casing and the tension/compression members 13, 15. In usage, the distal end of the catheter with electrode 1 is inserted in a guide tube placed in the patient's femoral vein; and, the portion of the catheter between electrode 1 and the pre-formed bend 12 is flexibly and temporarily resiliently flexed by the user to a position approximately parallel to that of the catheter casing 3 on the proximal side of the pre-formed bend 12 so as to permit insertion of the catheter into the proximal end of a guide tube inserted in the femoral vein. It will be understood however that during this insertion of the catheter into the guide tube placed in the vein; the pre-formed bend 12 remains in its approximately right angle configuration.

Figure 4:
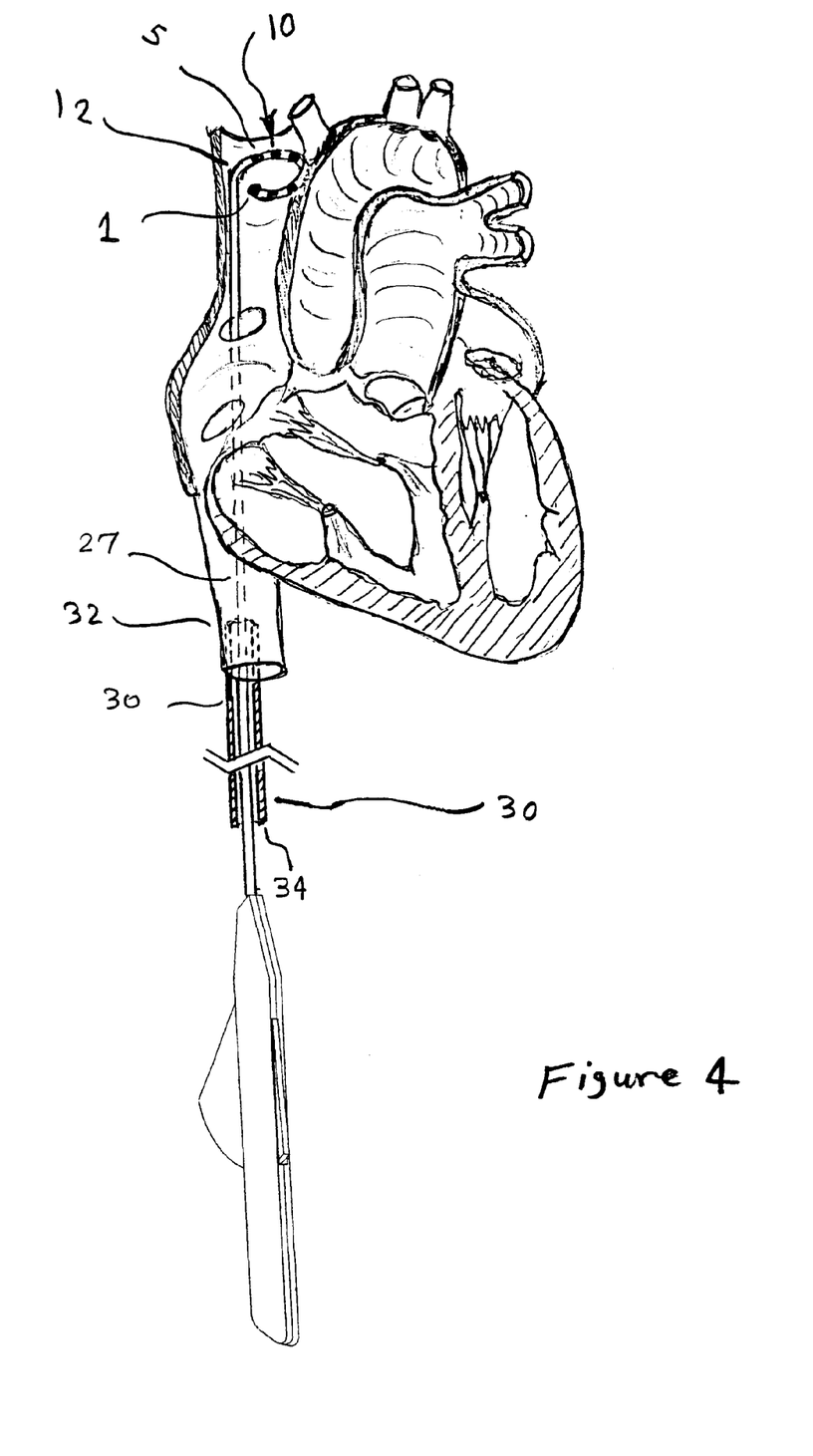
FIG. 4 is a perspective view of the heart with portion broken away to show the catheter with the halo formed on the distal end inserted through the femoral vein into the passage within the heart.
Figure 5:
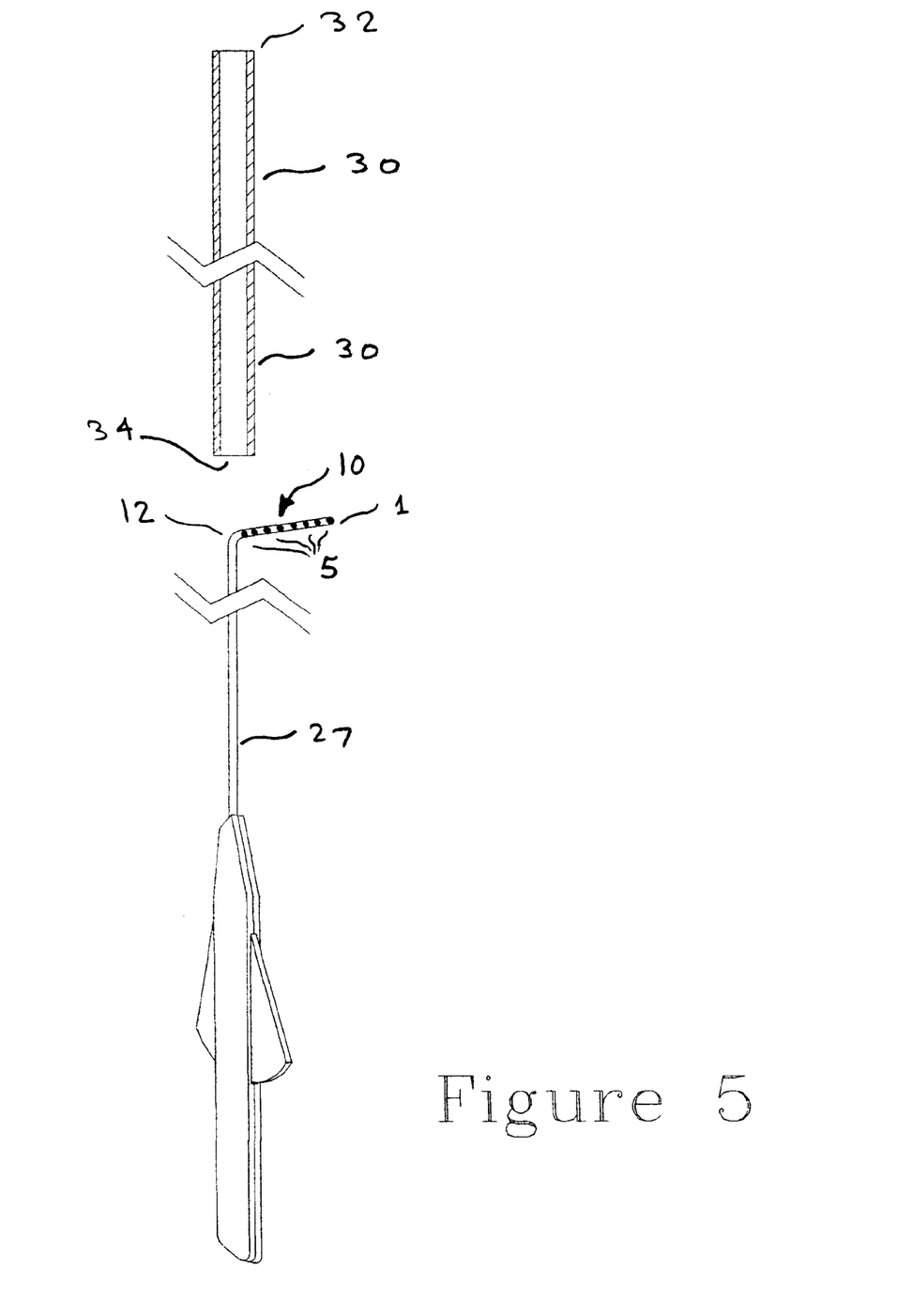
FIG. 5 is the view of the catheter of the present invention with the actuator and handle attached showing the distal end formed with the permanent bend prior to insertion in the guide tube.

Referring to FIG. 5 a guide tube is shown at 30 which is of the type insert able into the femoral vein of the patient with the distal end 32 thereof entering into the first chamber of the heart as shown in FIG. 4.

Figure 6:
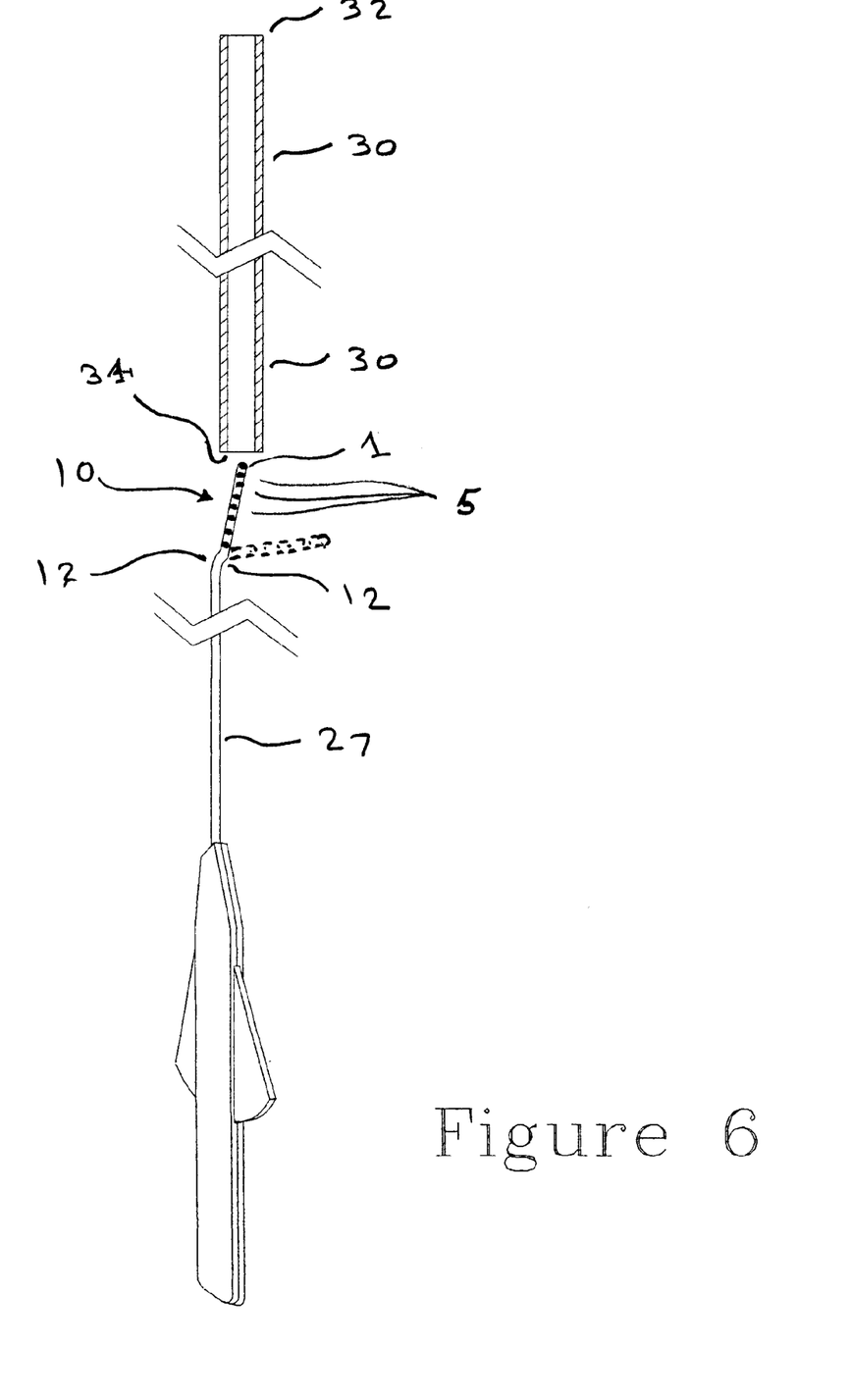
FIG. 6 is a view similar to FIG. 5 with the portion of the catheter distal end and preformed bend flexed for insertion in a guide tube.

In FIG. 6, the distal end of the catheter 10 with the preformed bend 12 therein is shown as disposed adjacent the proximal end 34 of the tube 30 prior to insertion therein.

Figure 7:
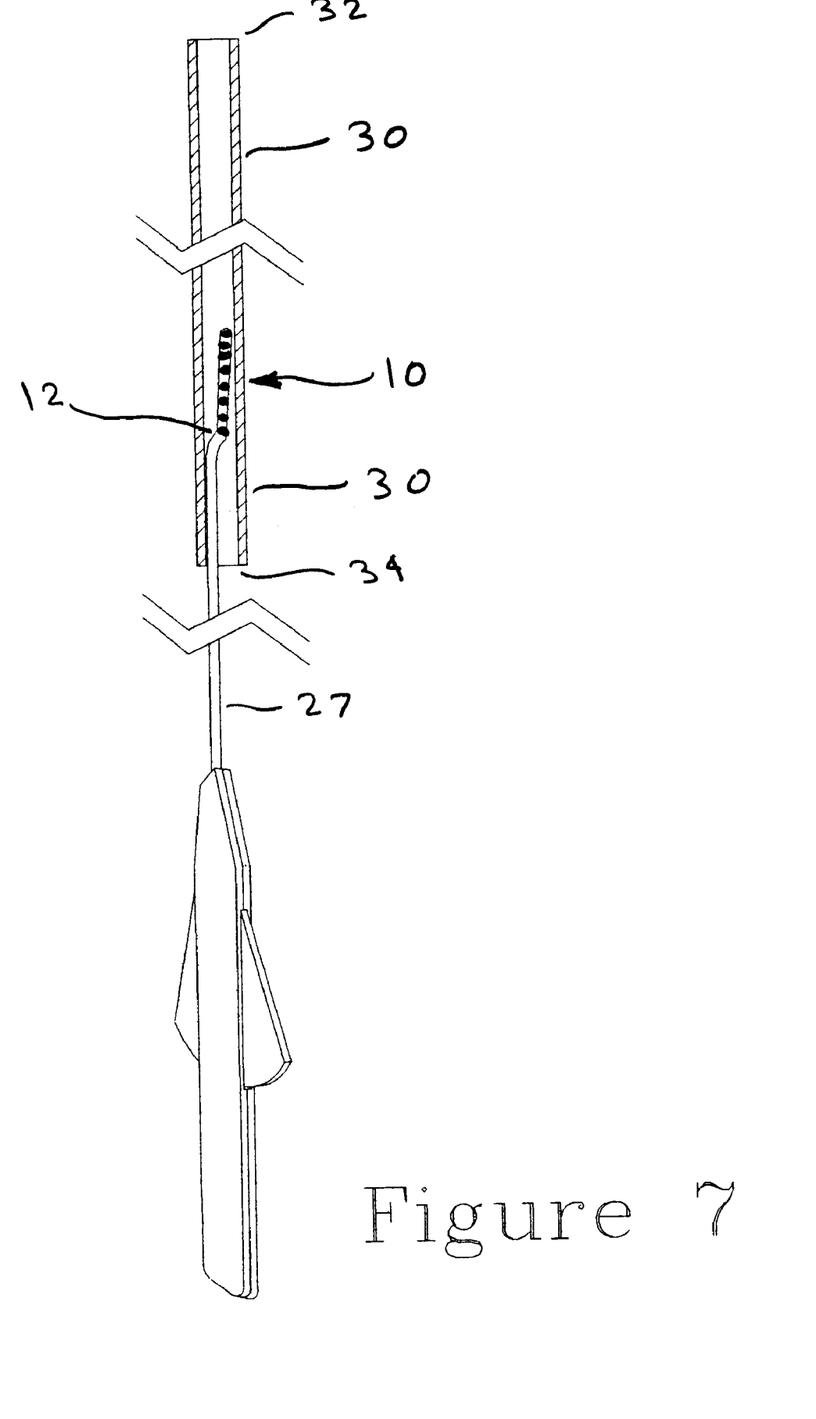
FIG. 7 is a view similar to FIG. 6 showing the distal end of the catheter of FIG. 6 inserted in the proximal end of a guide tube.
Figure 8:
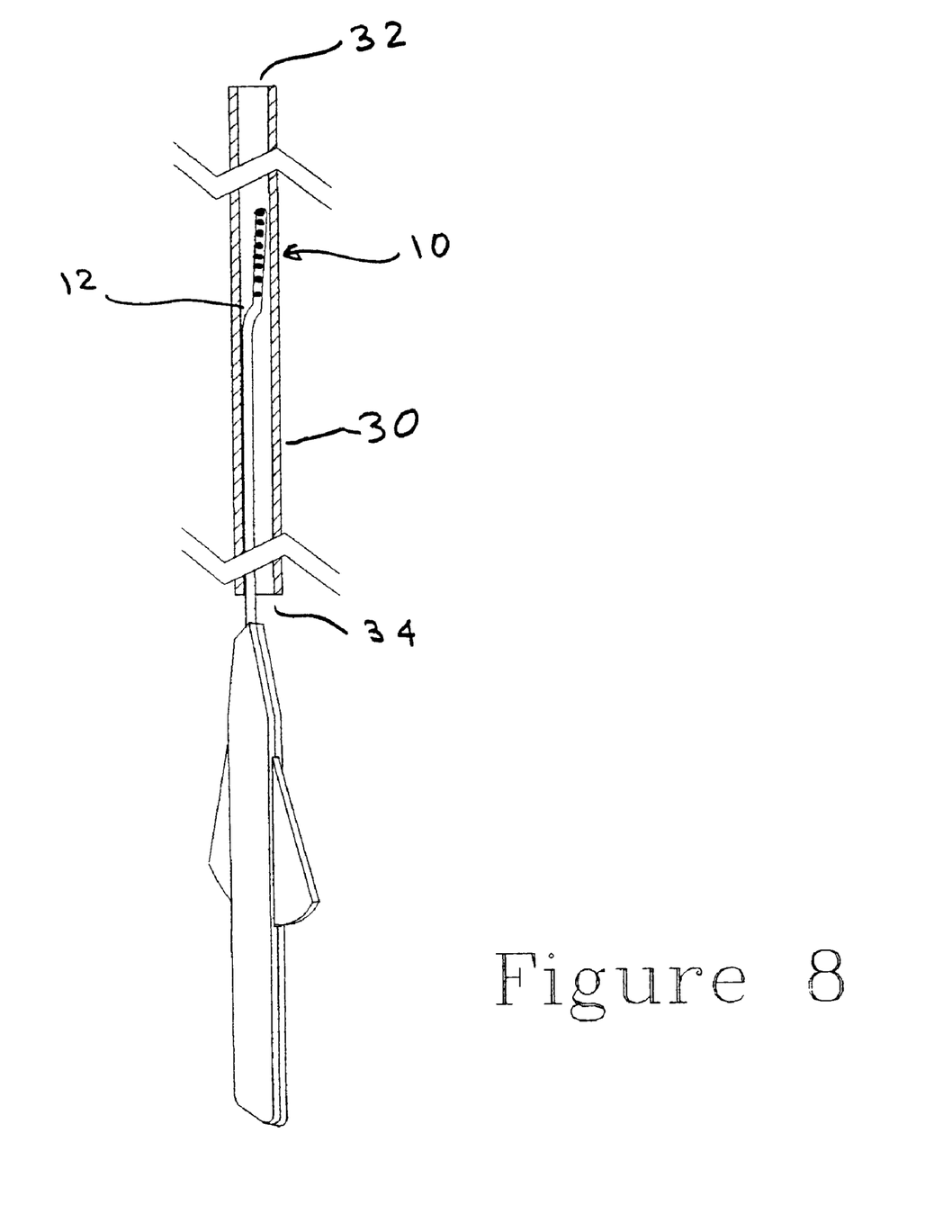
FIG. 8 is a view similar to FIG. 7 showing the distal end of the catheter further inserted into the guide tube.
Figure 9:
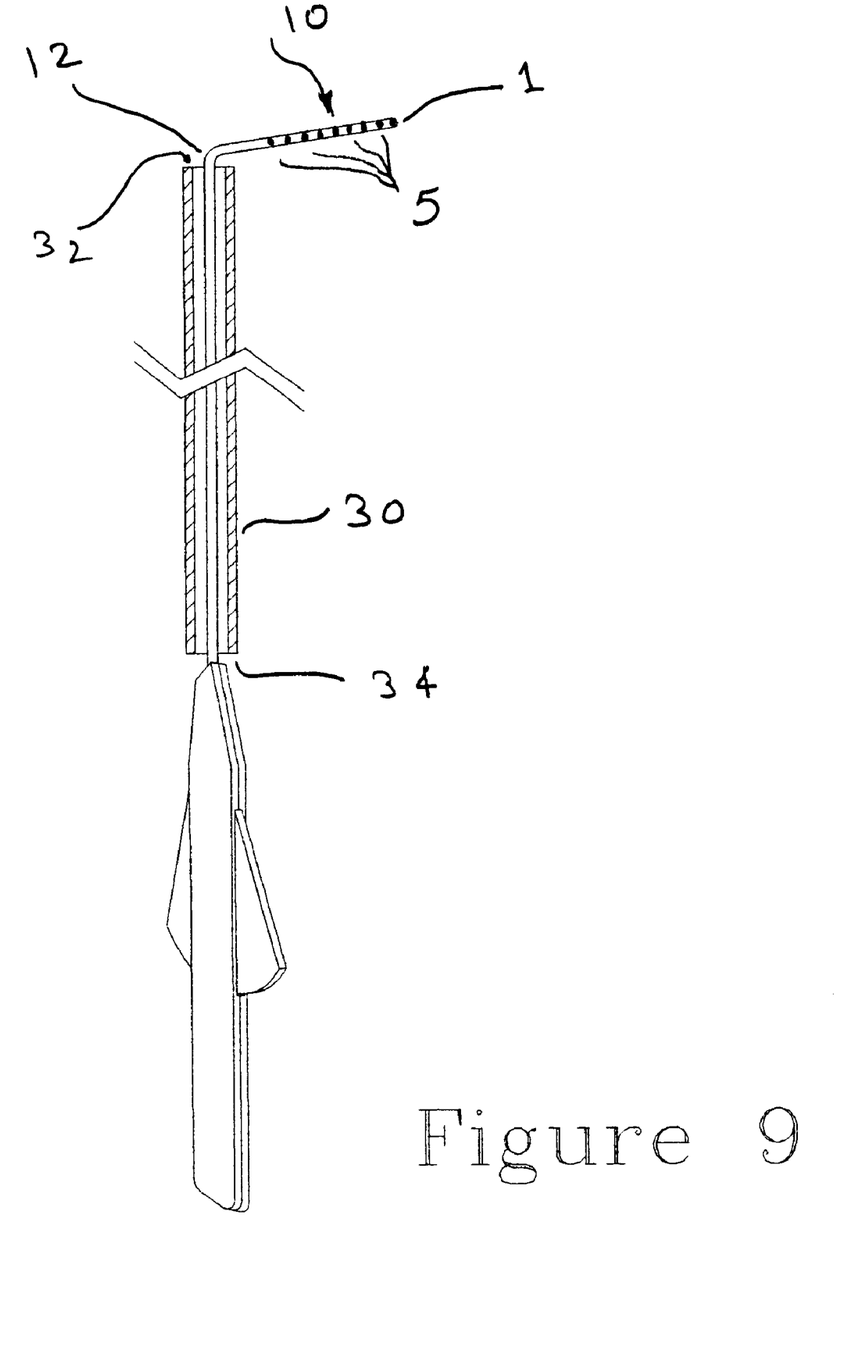
FIG. 9 is a view similar to FIG. 8 showing the distal end of the catheter including the preformed bend, extending exteriorly from the distal end of the guide tube; and, FIG. 10 is a view similar to FIG. 9 showing the distal end of the catheter curled to form a halo in a plane at right angles to the axis of the guide tube by movement of the actuator in the direction of the arrow.

Referring to FIG. 7, the distal end 10 of the catheter is manually deformed by the user from its initial position shown in dashed outline line to the position shown in solid line outline thereby forming a substantially "S" shaped offset in the catheter about the preformed bend 12 which remains formed in the catheter. With the end 10 held in the position shown in FIG. 6, the end 10 is inserted into the proximal end 34 of tube 30 and the catheter is pushed progressively through the guide tube as shown in FIGS. 7 and 8 until the distal end 10 thereof emerges from the distal end 32 of the guide tube 30 to return to its initial condition of FIG. 5 as shown in FIG. 9 except however with the end 10 disposed within a chamber in the heart as shown in FIG. 4.

Figure 10:
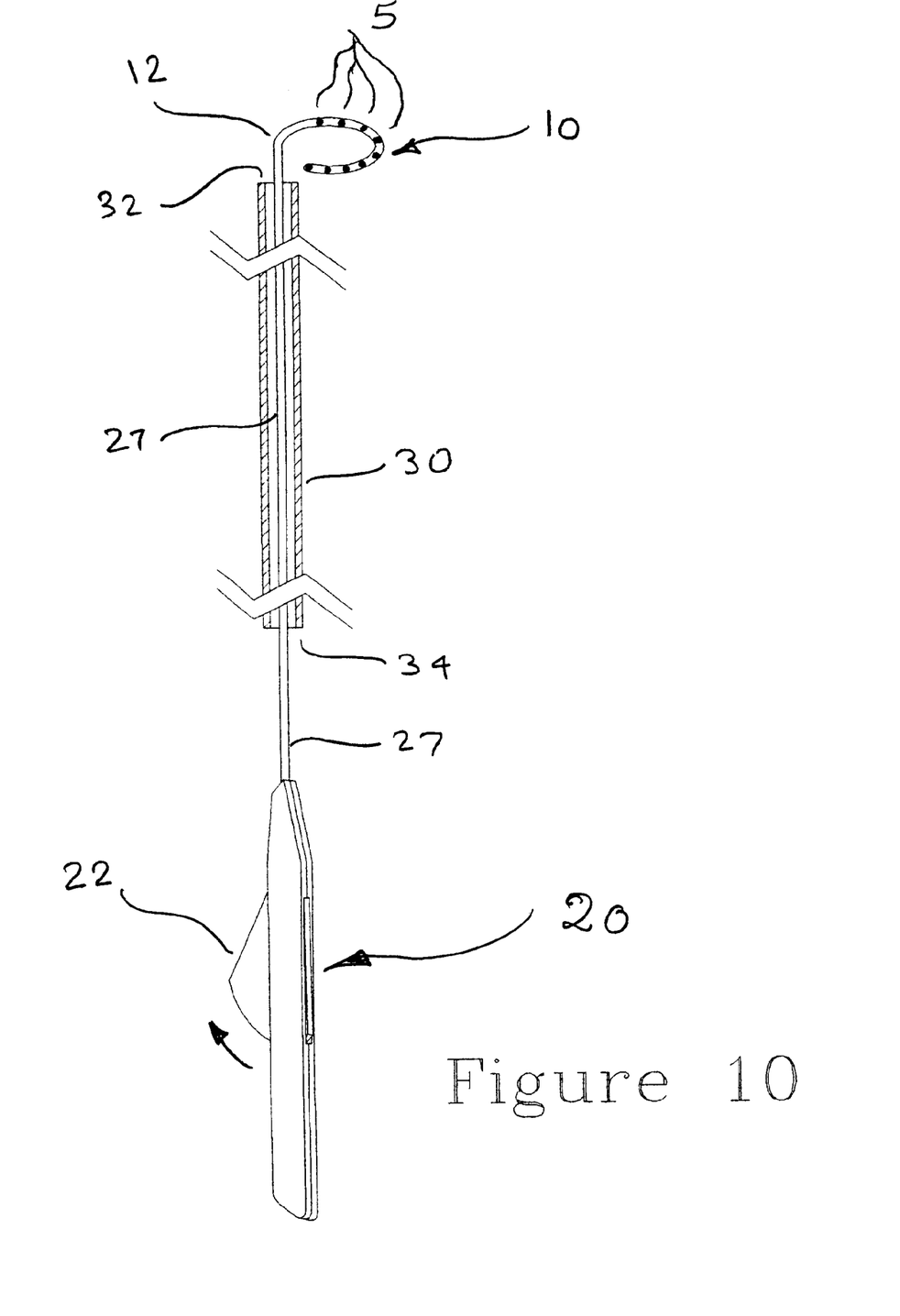

Referring now to FIG. 10, the actuator indicated generally at 20 has its movable member 22 moved in the direction shown by the black arrow in the FIG. 10 to cause the flattened ends 9, 11 of the tension/compression members to effect curling of the distal end 10 of the catheter to the halo configuration as shown in FIG. 10 except however now with the heart chamber as shown in FIG. 4.

Formation of the curled or halo configuration of the catheter as shown in FIG. 1c, FIG. 4, and FIG. 10 permits further placement of the catheter in the interior of the pulmonary vein of the heart for permitting either mapping of the electrical signals of the interior, or inner periphery, of the pulmonary vein or the performance of the ablation procedures by the introduction of radio-frequency electric current into the electrode 5.

Referring to FIG. 1b, the catheter is shown with the distal end partially curled by movement of the remote actuator member 22 on actuator 20.

Figure 3:
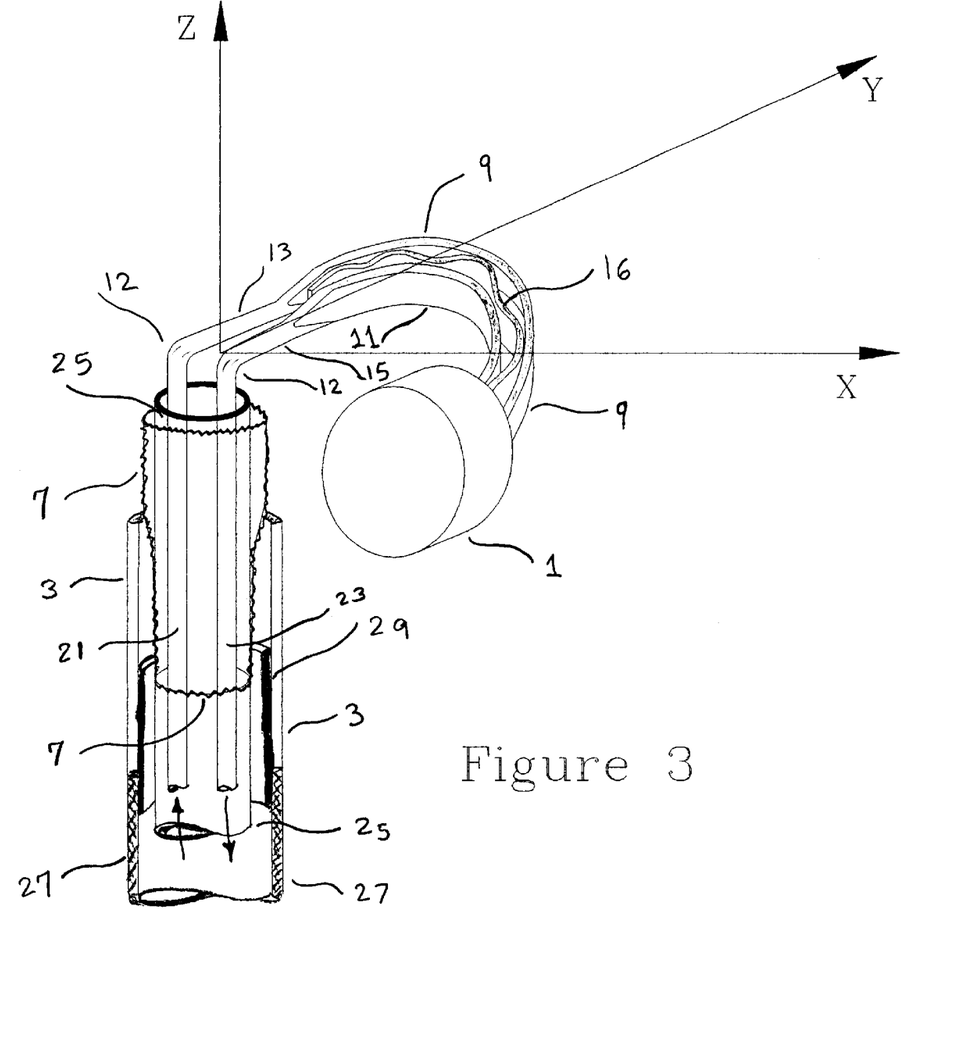
FIG. 3 is a view similar to FIG. 2 showing the distal end of the catheter, with casing removed, after actuation to form the halo.

Referring to FIGS. 1c and 10, the catheter of the present invention is shown in the fully looped or curled into a "halo" configuration where the pre-formed bend 12 formed about the X axis shown in FIG. 2 is retained; and, the distal portion of the catheter between distal electrode 1 and the pre-formed bend 12 has been flexibly curled, by the movement of the tension/compression members 21, 23, as shown by the black arrows in FIG. 3, to cause the distal portion of the catheter to form a loop or 270 degree bend about the Z axis, or in other words forming a loop in X–Y plane with reference to the axes shown in FIG. 3. As shown in FIG. 1c, the catheter is capable of bi-directional curling by movement of the remote actuator in opposite directions.

In the present practice of the invention, the outer diameter of the catheter casing is in the same range of about 0.062 inches to 0.092 inches (1.6 mm to 2.3 mm); and, the ring electrodes 5 are spaced about 0.080 inches to 0.200 inches (2 mm to 5 mm) apart along the axis of the casing. In the present practice of the invention the catheter has accommodated 11 ring electrodes in addition to the distal electrode.

In the present practice of the invention, a catheter having a casing diameter in the range of about 0.062 inches to 0.092 inches (1.6 mm to 2.3 mm) is capable of being curled into a halo having an inside diameter as small as 0.400 inches (10 mm) when the catheter is flexibly deformed by movement of the manual actuator 22 to move the tension/compression members 15, 17.

Although the invention has been described here and above with respect to the illustrated embodiments, it will be understood that the invention is capable of modification and variation and is limited only by the scope of the following claims.

What is claimed:

1. An electrophysiology/ablation catheter comprising:
   a) an elongated flexible tubular casing having a proximal end, a distal end and a plurality of spaced electrodes disposed at the distal end of said casing, said tubular casing having a pre-formed bend therein adjacent a proximal most one end of said spaced electrodes;
   b) a pair of tension/compression members disposed in side-by-side relationship and extending through said casing from a point of attachment adjacent said distal end to said proximal end of said casing, wherein at least one of said pair of tension/compression members includes a pre-formed bend aligned with the pre-formed bend of said tubular casing;
   c) an electrical lead connected to each of said electrodes and extending through the tubular casing to the proximal end thereof, said lead adapted for external connection; and
   d) an actuator connected to a proximal end of said tension/compression members and operable upon user movement to effect tensioning of one of said pair of tension/compression members and simultaneously compressing the other of said tension/compression members to cause displacement of said distal end of said casing toward an axis defined by the proximal end of said tubular casino while retaining said pre-formed bend in said tubular casing.

2. The catheter defined in claim 1, wherein said user movement of said actuator effects said displacement of said distal end of said casing in a curvature of at least 270 degrees in a plane substantially normal to the plane of said pre-formed bend.

3. The catheter defined in claim 1, wherein said pair of tension/compression members each have a portion thereof adjacent said distal end of said casing formed to have a flattened transverse section with the balance thereof circular.

4. A method of disposing in vivo an electrophysiology/ablation catheter in a passage in the heart comprising:
   a) providing an elongated tubular catheter having a pre-formed bend, a proximal portion aligned substantially along a first axis and a distal portion disposed on an opposite side of the pre-formed bend, the catheter also having a pair of tension/compression members in said tubular catheter and an actuator connected to said tension/compression members at an end of said catheter;
   b) moving said actuator and tensioning one of said tension/compression members and simultaneously compressing the other of said pair and whereby the distal portion of said tubular catheter moves toward the first axis while retaining the pie-formed bend; and,
   c) disposing said catheter in said heart passage.

5. The method defined in claim 4, wherein said step of moving includes curling said distal portion of said catheter at least 270 degrees.

6. An electrophysiology/ablation catheter comprising:
   a) an elongated flexible tubular casing having a proximal end, a distal end and a plurality of spaced electrodes disposed at the distal end, said casing having a pre-formed bend therein adjacent a proximal most one end of the spaced electrodes, wherein the pre-formed bend has a radius of about the same size as a transverse dimension of said tubular casing;
   b) a pair of tension/compression members disposed in side-by-side relationship and extending through said casing from a point of attachment adjacent the distal end to the proximal end of said casing;

c) an electrical lead connected to each of the electrodes and extending through said casing to the proximal end thereof, said lead adapted for external connection; and d) an actuator connected to a proximal end of said tension/compression members and operable upon user movement to effect tensioning of one of said pair of tension/compression members and simultaneously compressing the other of said tension/compression members to cause lateral displacement of the distal end of said casing substantially at right angle to the plane of said pre-formed bend.

7. The catheter of claim 6, wherein said pair of tension/compression members each have a portion thereof adjacent said distal end of said casing formed to have a flattened transverse section with the balance thereof circular.

8. An electrophysiology/ablation catheter comprising:

a) an elongated flexible tubular casing having a proximal end, a distal end and a plurality of spaced electrodes disposed at the distal end, said tubular casing having a pre-formed bend therein adjacent a proximal most one end of said spaced electrodes;

b) a pair of tension/compression members disposed in side-by-side relationship and extending through said casing from a point of attachment adjacent the distal end to the proximal end of said casing;

c) an electrical lead connected to each of the electrodes and extending through said casing to the proximal end thereof, said lead adapted for external connection; and d) a means for actuating said tension/compression members connected to a proximal end of said tension/compression members and operable upon user movement to effect tensioning of one of said pair of tension/compression members and simultaneously compressing the other of said tension/compression members to cause lateral displacement of the distal end of said casing substantially at right angle to the plane of said pre-formed bend, wherein the lateral displacement of the distal end of said casing comprises a curvature having a radius as small as 5 multiples of the transverse dimensions of said casing.

9. The catheter of claim 8, wherein said pair of tension/compression members each have a portion thereof adjacent said distal end of said casing formed to have a flattened transverse section with the balance thereof circular.

10. An electrophysiology/ablation catheter comprising:

a) an elongated flexible tubular casing having a proximal end, a distal end and a plurality of spaced electrodes disposed at the distal end, said tubular casing having a pre-formed bend therein adjacent a proximal most one end of said spaced electrodes;

b) a pair of tension/compression members disposed in side-by-side relationship and extending through said casing from a point of attachment adjacent the distal end to the proximal end of said casing, wherein said pair of tension/compression members each have a first portion thereof adjacent the distal end of said casing formed to have a flattened transverse section, and a second portion located in the region of the pre-formed bend formed to have circular cross-section oriented substantially at right angle to the first portion with the balance thereof circular;

c) an electrical lead connected to each of the electrodes and extending through said casing to the proximal end thereof, said lead adapted for external connection; and d) an actuator connected to a proximal end of said tension/compression members and operable upon user movement to effect tensioning of one of said pair of tension/compression members and simultaneously compressing the other of said tension/compression members to cause lateral displacement of the distal end of said casing substantially at right angle to the plane of said pre-formed bend.

11. An electrophysiology/ablation catheter comprising:

a) an elongated flexible tubular casing having a proximal end, a distal end and a plurality of spaced electrodes disposed at the distal end, said tubular casing having a pre-formed bend therein adjacent a proximal most one end of said spaced electrodes;

b) a pair of tension/compression members disposed in side-by-side relationship and extending through said casing from a point of attachment adjacent the distal end to the proximal end of said casing, wherein said tension/compression members have a transversely resilient spacer disposed therebetween proximal the distal end of said casing;

c) an electrical lead connected to each of the electrodes and extending through said casing to the proximal end thereof, said lead adapted for external connection; and d) an actuator connected to a proximal end of said tension/compression members and operable upon user movement to effect tensioning of one of said pair of tension/compression members and simultaneously compressing the other of said tension/compression members to cause lateral displacement of the distal end of said casing substantially at right angle to the plane of said pre-formed bend.

12. The catheter of claim 11, wherein said pair of tension/compression members each have a portion thereof adjacent said distal end of said casing formed to have a flattened transverse section with the balance thereof circular.

13. A method of disposing in vivo an electrophysiology/ablation catheter in a passage in the heart comprising:

a) providing an elongated tubular catheter aligned substantially along an axis having a pair of tension/compression members in said tubular catheter and an actuator connected to said tension/compression members at an end of said catheter;

b) moving said actuator and tensioning one of said tension/compression members and simultaneously compressing the other of said pair and curling a distal end of said tubular catheter in a loop configuration in a plane substantially normal to the axis of said tubular catheter, the loop configuration having a radius of curvature as small as 5 multiples of a transverse dimension of said tubular catheter; and, c) disposing said loop configuration in said heart passage and disposing said distal end in circumferential directions about an inner periphery of said heart passage.

* * * * *

UNITED STATES PATENT AND TRADEMARK OFFICE
CERTIFICATE OF CORRECTION

PATENT NO. : 6,728,563 B2
DATED : April 27, 2004
INVENTOR(S) : Rassoll Rashidi

It is certified that error appears in the above-identified patent and that said Letters Patent is hereby corrected as shown below:

Title page,
Item [54], Title, reads "ELECTROPHYSIOLOGY/ABLATION CATHETER HAVING "HALO" CONFIGURATION" should read
-- ELECTROPHYSIOLOGY/ABLATION CATHETER HAVING LARIAT CONFIGURATION --

Column 1,
Line 32, "patent '024" should read -- '024 patent --

Column 2,
Line 43, "450º" should read -- 45º --

Column 3,
Line 26, "preformed" should read -- pre-formed --

Column 5,
Line 2, "preformed" should read -- pre–formed --
Line 8, "preformed" should read -- pre-formed --

Column 6,
Line 26, "casino" should read -- casing --

Signed and Sealed this

Twenty-eighth Day of June, 2005

JON W. DUDAS
*Director of the United States Patent and Trademark Office*